US010159447B2

(12) United States Patent
Klein et al.

(10) Patent No.: US 10,159,447 B2
(45) Date of Patent: Dec. 25, 2018

(54) ALIGNMENT CT

(71) Applicant: Covidien LP, Mansfield, MA (US)

(72) Inventors: Eyal Klein, Hertzliya (IL); Benjamin Greenburg, Hod Hasharon (IL)

(73) Assignee: COVIDIEN LP, Mansfield, MA (US)

( * ) Notice: Subject to any disclaimer, the term of this patent is extended or adjusted under 35 U.S.C. 154(b) by 556 days.

(21) Appl. No.: 14/790,395

(22) Filed: Jul. 2, 2015

(65) Prior Publication Data
US 2016/0000303 A1    Jan. 7, 2016

Related U.S. Application Data

(60) Provisional application No. 62/020,245, filed on Jul. 2, 2014.

(51) Int. Cl.
*A61B 1/04* (2006.01)
*A61B 6/03* (2006.01)
*A61B 6/12* (2006.01)
*A61B 1/00* (2006.01)
*A61B 6/00* (2006.01)
(Continued)

(52) U.S. Cl.
CPC ............ *A61B 6/032* (2013.01); *A61B 1/0005* (2013.01); *A61B 6/12* (2013.01); *A61B 6/488* (2013.01); *A61B 34/20* (2016.02); *A61B 2034/2051* (2016.02); *A61B 2090/365* (2016.02)

(58) Field of Classification Search
CPC ....... A61B 1/2676; A61B 6/465; A61B 6/466; A61B 6/5223; A61B 34/10; A61B 2034/107; A61B 2034/2051

USPC ......... 600/118, 117, 114; 378/98.5; 345/419, 345/420; 606/1; 382/103
See application file for complete search history.

(56) References Cited

U.S. PATENT DOCUMENTS

| 5,227,985 | A | * | 7/1993 | DeMenthon | ............ | G01S 5/163 |
| | | | | | | 345/158 |
| 5,237,647 | A | * | 8/1993 | Roberts | ................... | G06F 3/038 |
| | | | | | | 178/18.01 |

(Continued)

FOREIGN PATENT DOCUMENTS

| JP | 2001518351 A | 10/2001 |
| JP | 2008054763 A | 3/2008 |

(Continued)

OTHER PUBLICATIONS

Extended European Search report for application No. 15815034.2 dated Mar. 8, 2018, 7 pages.

*Primary Examiner* — Timothy J Neal
*Assistant Examiner* — Jae Woo

(57) ABSTRACT

Methods and systems for navigating to a target through a patient's bronchial tree are disclosed including a bronchoscope, a probe insertable into a working channel of the bronchoscope including a location sensor, and a workstation in operative communication with the probe and the bronchoscope the workstation including a user interface that guides a user through a navigation plan and is configured to present a three-dimensional (3D) view for displaying a 3D rendering of the patient's airways and a corresponding navigation plan, a local view for assisting the user in navigating the probe through peripheral airways of the patient's bronchial tree to the target, and a target alignment view for assisting the user in aligning a distal tip of the probe with the target.

14 Claims, 4 Drawing Sheets

(51) Int. Cl.
*A61B 34/20* (2016.01)
*A61B 90/00* (2016.01)

(56) References Cited

U.S. PATENT DOCUMENTS

| | | | |
|---|---|---|---|
| 5,297,061 A * | 3/1994 | Dementhon | G06F 3/0346 345/156 |
| 5,364,392 A | 11/1994 | Warner et al. | |
| 5,685,839 A | 11/1997 | Edwards et al. | |
| 5,995,107 A * | 11/1999 | Berteig | G06T 19/20 345/420 |
| 6,262,734 B1 * | 7/2001 | Ishikawa | G06F 3/04815 345/440 |
| 6,346,938 B1 * | 2/2002 | Chan | G06F 3/04815 345/419 |
| 6,427,089 B1 | 7/2002 | Knowlton | |
| 6,575,969 B1 | 6/2003 | Rittman, III et al. | |
| 6,689,127 B1 | 2/2004 | Gough et al. | |
| 7,113,832 B2 | 9/2006 | Longo | |
| 7,822,461 B2 * | 10/2010 | Geiger | G06T 19/003 600/109 |
| 8,585,598 B2 * | 11/2013 | Razzaque | A61B 8/4245 600/411 |
| 8,641,621 B2 * | 2/2014 | Razzaque | A61B 34/20 600/407 |
| 8,700,132 B2 * | 4/2014 | Ganatra | A61B 34/20 600/424 |
| 8,821,376 B2 * | 9/2014 | Tolkowsky | A61B 1/0052 600/101 |
| 9,226,687 B2 * | 1/2016 | Soper | A61B 1/0008 |
| 2002/0026187 A1 | 2/2002 | Swanson | |
| 2002/0193677 A1 * | 12/2002 | Thornton | G06F 17/3028 600/407 |
| 2004/0049254 A1 | 3/2004 | Longo | |
| 2005/0080333 A1 | 4/2005 | Piron et al. | |
| 2005/0245920 A1 | 11/2005 | Vitullo et al. | |
| 2006/0004351 A1 | 1/2006 | Arless et al. | |
| 2006/0033728 A1 * | 2/2006 | Sako | A61B 6/463 345/204 |
| 2006/0235671 A1 * | 10/2006 | Kirchberg | G06F 19/321 703/11 |
| 2006/0239400 A1 * | 10/2006 | Sukovic | A61B 6/032 378/38 |
| 2007/0167714 A1 * | 7/2007 | Kiraly | A61B 1/2676 600/407 |
| 2007/0257903 A1 * | 11/2007 | Gutierrez | G06T 17/05 345/419 |
| 2007/0288207 A1 * | 12/2007 | Backe | G06F 17/5004 703/1 |
| 2008/0033424 A1 | 2/2008 | van der Weide et al. | |
| 2009/0003668 A1 * | 1/2009 | Matsumoto | A61B 5/055 382/128 |
| 2009/0012390 A1 * | 1/2009 | Pescatore | A61B 6/12 600/425 |
| 2009/0030306 A1 * | 1/2009 | Miyoshi | A61B 1/005 600/424 |
| 2009/0099452 A1 * | 4/2009 | Hashimoto | A61B 8/463 600/443 |
| 2010/0312094 A1 * | 12/2010 | Guttman | A61B 5/415 600/411 |
| 2011/0118723 A1 | 5/2011 | Turner et al. | |
| 2011/0237897 A1 * | 9/2011 | Gilboa | A61B 1/00154 600/202 |
| 2012/0059248 A1 * | 3/2012 | Holsing | A61B 1/2676 600/424 |
| 2012/0259204 A1 * | 10/2012 | Carrat | A61B 5/061 600/414 |
| 2012/0259326 A1 | 10/2012 | Brannan et al. | |
| 2013/0165854 A1 * | 6/2013 | Sandhu | A61B 6/12 604/95.01 |
| 2013/0197357 A1 * | 8/2013 | Green | A61B 8/0841 600/424 |
| 2013/0223702 A1 * | 8/2013 | Holsing | A61B 5/113 382/128 |
| 2013/0281838 A1 * | 10/2013 | Trumer | A61B 6/12 600/424 |
| 2014/0051986 A1 * | 2/2014 | Zhao | A61B 5/066 600/424 |
| 2014/0088457 A1 * | 3/2014 | Johnson | A61B 17/12104 600/567 |
| 2014/0187949 A1 * | 7/2014 | Zhao | A61B 8/12 600/443 |
| 2014/0267031 A1 * | 9/2014 | Huebner | G06F 3/0346 345/158 |
| 2014/0276005 A1 * | 9/2014 | Forsyth | A61B 5/0071 600/424 |
| 2014/0276033 A1 * | 9/2014 | Brannan | A61B 6/03 600/431 |
| 2014/0282216 A1 * | 9/2014 | Baker | G06F 19/3406 715/781 |
| 2014/0359535 A1 * | 12/2014 | Little | G06F 3/04886 715/848 |
| 2015/0305650 A1 * | 10/2015 | Hunter | A61B 1/0005 600/424 |

FOREIGN PATENT DOCUMENTS

| | | |
|---|---|---|
| JP | 2011516184 | 5/2011 |
| JP | 2012187405 | 10/2012 |
| WO | 2008095068 A1 | 8/2008 |
| WO | 2011063061 A2 | 5/2011 |
| WO | 2012071388 A2 | 5/2012 |
| WO | 2013080131 A1 | 6/2013 |
| WO | 2014025551 A1 | 2/2014 |

\* cited by examiner

ALIGNMENT CT

CROSS-REFERENCE TO RELATED APPLICATIONS

This application claims the benefit of, and priority to, U.S. Provisional Patent Application No. 62/020,245, filed on Jul. 2, 2014, the entire contents of which are incorporated herein by reference.

BACKGROUND

1. Technical Field

The present disclosure relates to systems and methods for internally guided navigation of catheters based on a three-dimensional model generated from CT image data.

2. Discussion of Related Art

Visualization techniques related to visualizing a patient's lungs have been developed so as to help clinicians perform diagnoses and/or surgeries on the patient's lungs. Visualization is especially important for identifying a location of a diseased region. Further, when treating the diseased region, additional emphasis is given to identification of the particular location of the diseased region so that a surgical operation is performed at the correct location.

In the past, scanned two-dimensional (2D) images of the lungs have been used to aid in visualization. In order to obtain the scanned 2D images, a patient undergoes multiple CT scans. In addition to using scanned 2D images, three-dimensional (3D) models may also be used to virtually navigate through the body. The use of 3D models for navigation is more complex than using 2D images. One of the challenges involves guiding a user to point the catheter to the target in 3D. Many views have been developed, some of them using multiple cross-sections, and a proposed view is designed to assist with guidance. However, when one tries to look through the whole volume from a point of view instead of looking at a cross-section, the view may be obstructed and objects, which are behind other objects, might not be seen. Methods have been developed to alleviate the obstructed view problem, such as adding transparency to some of the volume or highlighting farther objects. One of the known methods involves Maximum Intensity Projection (MIP) which is a volume rendering method for 3D data that projects in the visualization plane the voxels with maximum intensity that fall in the way of parallel rays traced from the viewpoint to the plane of projection. Thus, two MIP renderings from opposite viewpoints are symmetrical images if they are rendered using orthographic projection. However, when using MIP to align an electromagnetic navigation catheter towards a specific point (lesion), objects which are "behind" the lesion, such as ribs or other non-soft tissue, might be shown instead of the lesion.

SUMMARY

In an embodiment, the present disclosure discloses a system for navigating to a target through a patient's bronchial tree. The system includes a bronchoscope configured for insertion into the patient's bronchial tree where the bronchoscope defines a working channel, a probe insertable into the working channel of the bronchoscope and configured to navigate through the patient's bronchial tree, the probe including a location sensor, and a workstation in operative communication with the probe and the bronchoscope. The workstation includes a memory and at least one processor, the memory storing a navigation plan and a program that, when executed by the processor, presents a user interface that guides a user through the navigation plan. The user interface presents a three-dimensional (3D) view for displaying a 3D rendering of the patient's airways and a corresponding navigation plan, a local view for assisting the user in navigating the probe through peripheral airways of the patient's bronchial tree to the target, and a target alignment view for assisting the user in aligning a distal tip of the probe with the target.

In an aspect, the processor executes a maximum intensity projection (MIP) algorithm for a range from a distal tip of the location sensor.

In another aspect, the range is predetermined.

In yet another aspect, the range is dynamically calculated based on a location of the target.

In an aspect, the MIP algorithm causes the target to be displayed in a maximal surface size in the target alignment view.

In another aspect, the MIP algorithm highlights the target and filters out densities of other tissue near the target.

In an aspect, the target alignment view presents a marking overlaid on the target.

In another aspect, the target alignment view presents a crosshair to assist alignment to a center of the target.

In yet another aspect, the target alignment view presents a distance from a tip of the location sensor to the target.

In another embodiment, the present disclosure discloses a system for navigating to a target through a patient's bronchial tree. The system includes a bronchoscope configured for insertion into the patient's bronchial tree where the bronchoscope defines a working channel, a probe insertable into the working channel of the bronchoscope and configured to navigate through the patient's bronchial tree, the probe including a location sensor, and a workstation in operative communication with the probe and the bronchoscope. The workstation includes a memory and at least one processor, the memory storing a navigation plan and a program that, when executed by the processor, presents a user interface that guides a user through the navigation plan, the user interface configured to present a target alignment view for assisting the user in aligning a distal tip of the probe with the target. The processor executes a maximum intensity projection (MIP) algorithm for a limited range from a distal tip of the location sensor.

In an aspect, the limited range is predetermined.

In another aspect, the limited range is dynamically calculated based on a location of the target.

In an aspect, the MIP algorithm causes the target to be displayed in a maximal surface size in the target alignment view.

In another aspect, the MIP algorithm highlights the target and filters out densities of other tissue near the target.

In an aspect, the target alignment view presents a marking overlaid on the target.

In another aspect, the target alignment view presents a crosshair to assist alignment to a center of the target.

In yet another aspect, the target alignment view presents a distance from a tip of the location sensor to the target.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

Figure 1:
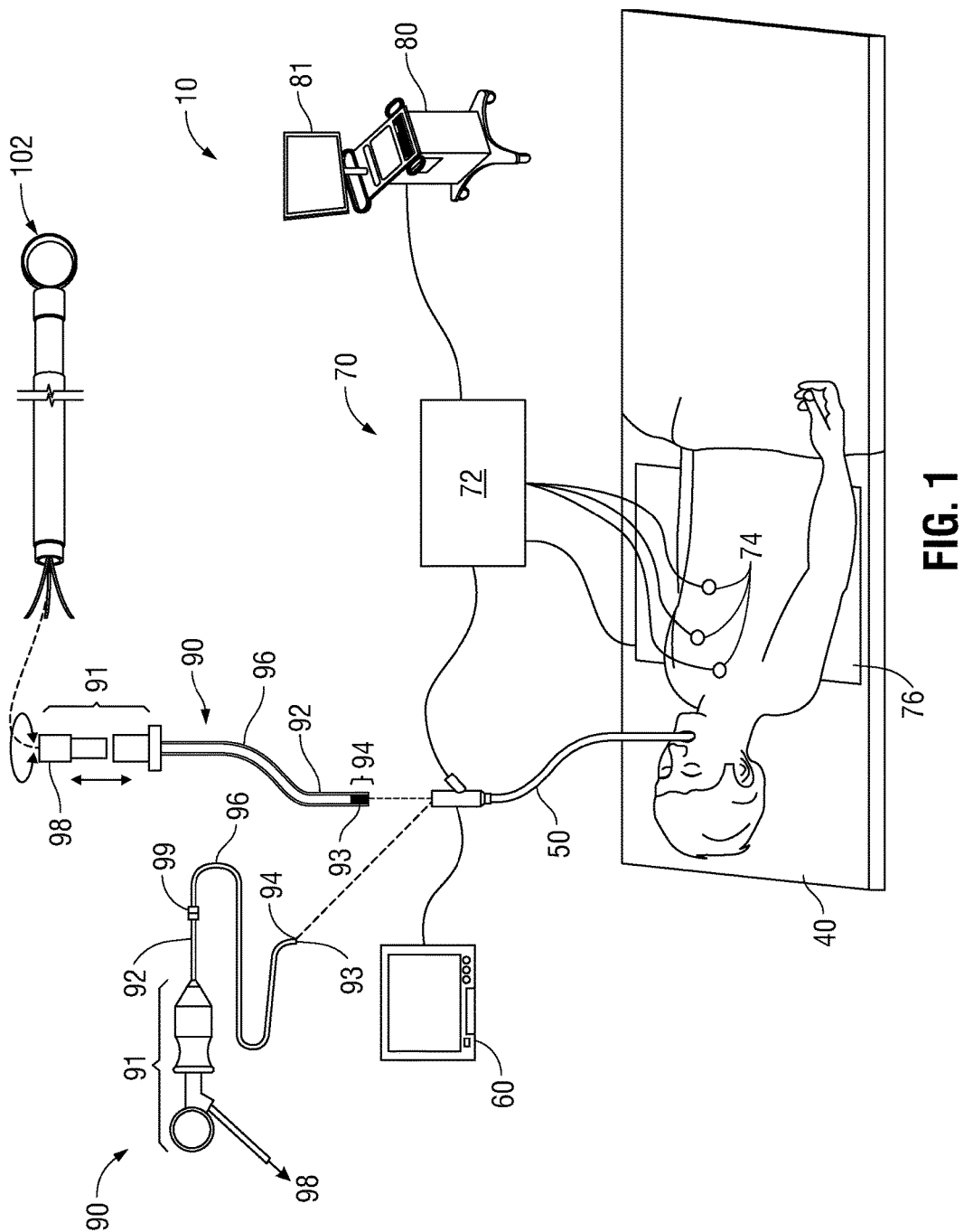
FIG. 1 is a perspective view of an electromagnetic navigation system in accordance with the present disclosure.

The present disclosure is related to devices, systems, and methods for internally guided navigation of catheters based on a three-dimensional model generated from CT image data to align the catheter toward a target area. In the present disclosure, the system provides a view with a defined section of volume based on a range from the catheter or a section of the volume in vicinity of a target area or lesion. Alignment of the catheter may be a necessary component of pathway planning for performing an ELECTROMAGNETIC NAVIGATION BRONCHOSCOPY® (ENB) procedure using an electromagnetic navigation (EMN) system.

An ENB procedure generally involves at least two phases: (1) planning a pathway to a target located within, or adjacent to, the patient's lungs; and (2) navigating a probe to the target along the planned pathway. These phases are generally referred to as (1) "planning" and (2) "navigation." The planning phase of an ENB procedure is more fully described in commonly-owned U.S. patent application Ser. Nos. 13/838,805; 13/838,997; and 13/839,224, all entitled "Pathway Planning System and Method," filed on Mar. 15, 2013, by Baker, the entire contents of which are hereby incorporated by reference. An example of the planning software can be found in commonly assigned U.S. Provision Patent Application No. 62/020,240 entitled "SYSTEM AND METHOD FOR NAVIGATING WITHIN THE LUNG" the entire contents of which are incorporated herein by reference.

Prior to the planning phase, the patient's lungs are imaged by, for example, a computed tomography (CT) scan, although additional applicable methods of imaging will be known to those skilled in the art. The image data assembled during the CT scan may then be stored in, for example, the Digital Imaging and Communications in Medicine (DICOM) format, although additional applicable formats will be known to those skilled in the art. The CT scan image data may then be loaded into a planning software application ("application") to be used during the planning phase of the ENB procedure.

Embodiments of the systems and methods are described with reference to the accompanying drawings. Like reference numerals may refer to similar or identical elements throughout the description of the figures. This description may use the phrases "in an embodiment," "in embodiments," "in some embodiments," or "in other embodiments," which may each refer to one or more of the same or different embodiments in accordance with the present disclosure.

With reference to FIG. 1, an electromagnetic navigation (EMN) system 10 is provided in accordance with the present disclosure. Among other tasks that may be performed using the EMN system 10 are planning a pathway to target tissue, navigating a positioning assembly to the target tissue, navigating a biopsy tool to the target tissue to obtain a tissue sample from the target tissue using the biopsy tool, and digitally marking the location where the tissue sample was obtained, and placing one or more echogenic markers at or around the target.

EMN system 10 generally includes an operating table 40 configured to support a patient; a bronchoscope 50 configured for insertion through the patient's mouth and/or nose into the patient's airways; monitoring equipment 60 coupled to bronchoscope 50 for displaying video images received from bronchoscope 50; a tracking system 70 including a tracking module 72, a plurality of reference sensors 74, and an electromagnetic field generator 76; a workstation 80 including software and/or hardware used to facilitate pathway planning, identification of target tissue, navigation to target tissue, and digitally marking the biopsy location FIG. 1 also depicts two types of catheter guide assemblies 90, 100. Both catheter guide assemblies 90, 100 are usable with the EMN system 10 and share a number of common components. Each catheter guide assembly 90, 100 includes a handle 91, which is connected to an extended working channel (EWC) 96. The EWC 96 is sized for placement into the working channel of a bronchoscope 50. In operation, a locatable guide (LG) 92, including an electromagnetic (EM) sensor 94, is inserted into the EWC 96 and locked into position such that the sensor 94 extends a desired distance beyond the distal tip 93 of the EWC 96. The location of the EM sensor 94, and thus the distal end of the EWC 96, within an electromagnetic field generated by the electromagnetic field generator 76 can be derived by the tracking module 72, and the workstation 80.

Figure 2:
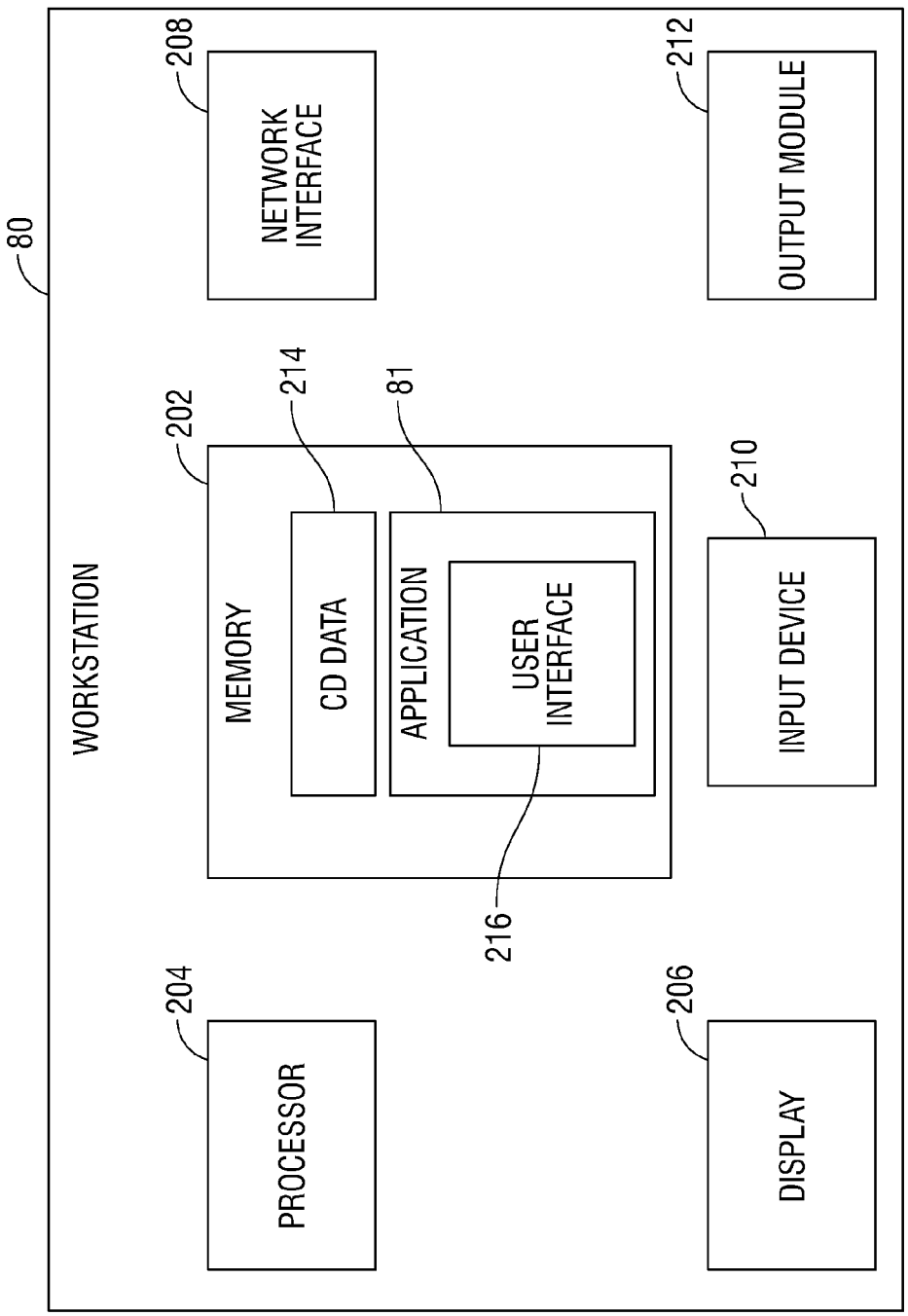
FIG. 2 is a schematic diagram of a workstation configured for use with the system of FIG. 1.

Turning now to FIG. 2, there is shown a system diagram of workstation 80. Workstation 80 may include memory 202, processor 204, display 206, network interface 208, input device 210, and/or output module 212. Workstation 80 implements the methods that will be described herein.

Figure 3:
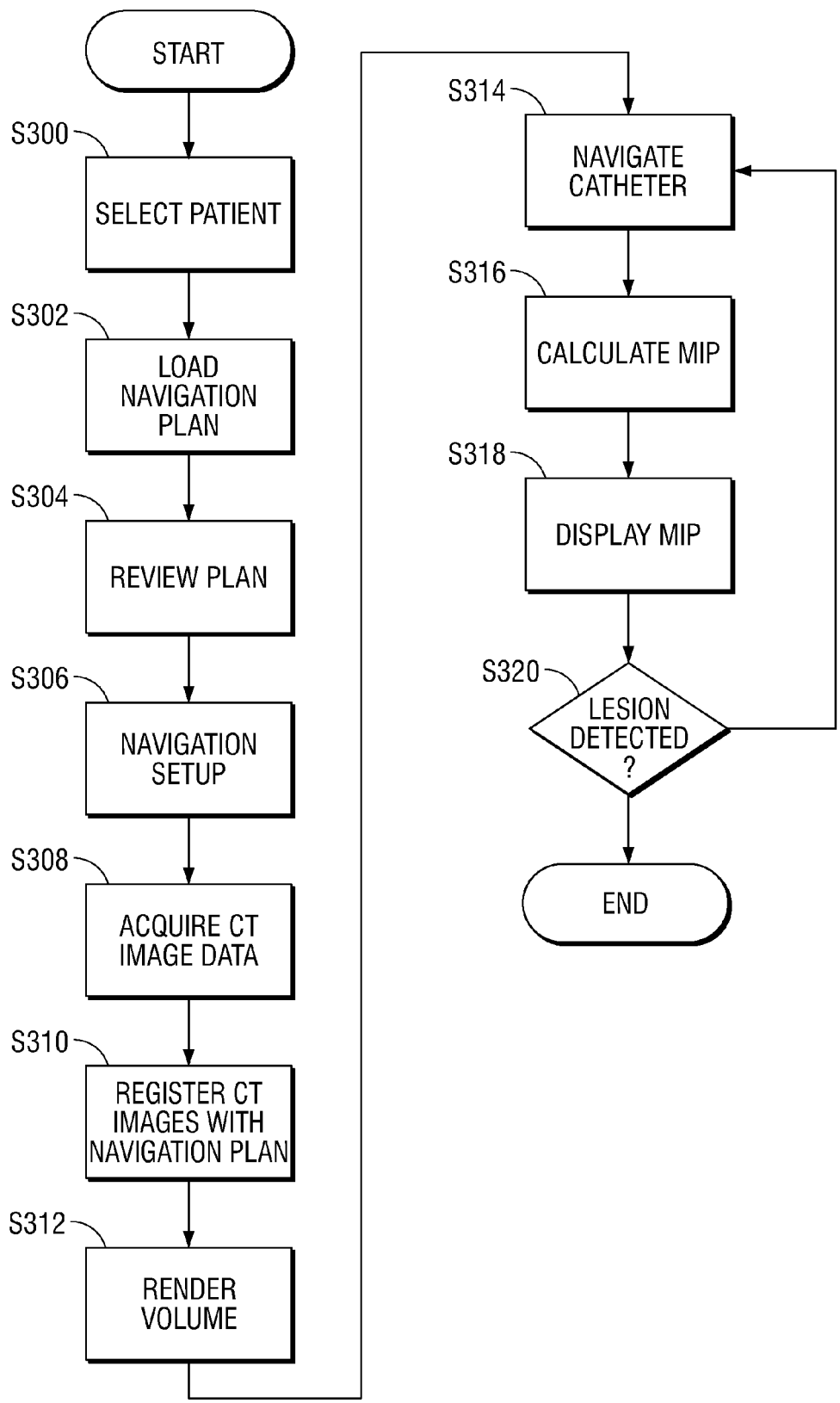
FIG. 3 is a flow chart illustrating a method of navigation in accordance with an embodiment of the present disclosure.

FIG. 3 depicts a method of navigation using the navigation workstation 80 and the user interface 216. In step S300 user interface 216 presents the clinician with a view (not shown) for the selection of a patient. The clinician may enter patient information such as, for example, the patient name or patient ID number, into a text box to select a patient on which to perform a navigation procedure. Alternatively, the patient may be selected from a drop down menu or other similar methods of patient selection. Once the patient has been selected, the user interface 216 presents the clinician with a view (not shown) including a list of available navigation plans for the selected patient. In step S302, the clinician may load one of the navigation plans by activating the navigation plan. The navigation plans may be imported from a procedure planning software and include CT images of the selected patient.

Once the patient has been selected and a corresponding navigation plan has been loaded, the user interface 216 presents the clinician with a patient details view (not shown) in step S304 which allows the clinician to review the selected patient and plan details. Examples of patient details presented to the clinician in the timeout view may include the patient's name, patient ID number, and birth date. Examples of plan details include navigation plan details, automatic registration status, and/or manual registration status. For example, the clinician may activate the navigation plan details to review the navigation plan, and may verify the availability of automatic registration and/or manual registration. The clinician may also activate an edit button (not shown) to edit the loaded navigation plan from the patient details view. Activating the edit button (not shown) of the loaded navigation plan may also activate the planning software described above. Once the clinician is satisfied that the patient and plan details are correct, the clinician proceeds to navigation setup in step S306. Alternatively, medical staff may perform the navigation setup prior to or concurrently with the clinician selecting the patient and navigation plan.

During navigation setup in step S306, the clinician or other medical staff prepares the patient and operating table by positioning the patient on the operating table over the electromagnetic field generator 76. The clinician or other medical staff position reference sensors 74 on the patient's chest and verify that the sensors are properly positioned, for example, through the use of a setup view (not shown) presented to the clinician or other medical staff by user interface 216. Setup view may, for example, provide the clinician or other medical staff with an indication of where the reference sensors 74 are located relative to the magnetic field generated by the transmitter mat 76. Patient sensors allow the navigation system to compensate for patient breathing cycles during navigation. The clinician also prepares LG 92, EWC 96, and bronchoscope 50 for the procedure by inserting LG 92 into EWC 96 and inserting both LG 92 and EWC 96 into the working channel of bronchoscope 50 such that distal tip 93 of LG 92 extends from the distal end of the working channel of bronchoscope 50. For example, the clinician may extend the distal tip 93 of LG 92 10 mm beyond the distal end of the working channel of bronchoscope 50.

Figure 4:
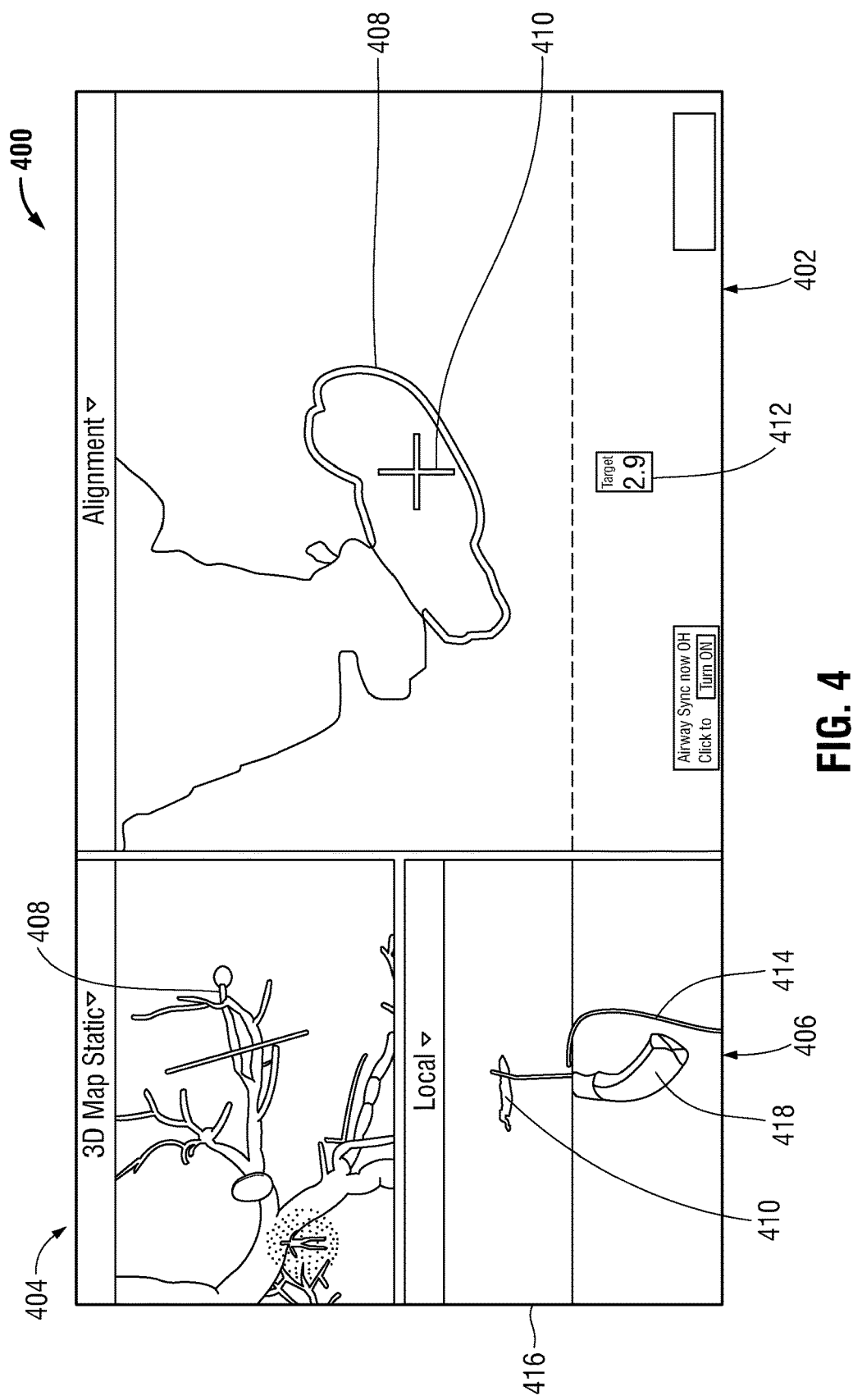
FIG. 4 is an illustration of a user interface of the workstation of FIG. 2 presenting a view for performing registration in accordance with the present disclosure.

Once setup is complete, the workstation 80 presents a view 400, as shown in FIG. 4, via the user interface 216. CT image data is acquired and displayed in alignment view 402 of view 400 in step 308. In step 310, the CT image data is registered with the selected navigation plan. An example method for registering images with a navigation plan is described in U.S. Provisional Patent Application Ser. No. 62/020,240 entitled "System and Method for Navigating Within the Lung," filed on Jul. 2, 2014, by Brown et al., the entire contents of each of which are incorporated herein by reference and useable with the EMN system 10 as described herein.

In step s312, workstation 80 performs a volume rendering algorithm based on the CT image data included in the navigation plan and position signals from sensor 94 to generate a 3D view 404 of the walls of the patient's airways as shown in FIG. 4. The 3D view 404 uses a perspective rendering that supports perception of advancement when moving closer to objects in the volume. The 3D view 404 also presents the user with a navigation pathway providing an indication of the direction along which the user will need to travel to reach the lesion 410. The navigation pathway may be presented in a color or shape that contrasts with the 3D rendering so that the user may easily determine the desired path to travel. Workstation 80 also presents a local view 406 as shown in FIG. 4 that includes a slice of the 3D volume located at and aligned with the distal tip 93 of LG 92. Local view 406 shows the lesion 410 and the navigation pathway 414 overlaid on slice 416 from an elevated perspective. The slice 416 that is presented by local view 406 changes based on the location of EM sensor 94 relative to the 3D volume of the loaded navigation plan. Local view 406 also presents the user with a virtual representation of the distal tip 93 of LG 92 in the form of a virtual probe 418. The virtual probe 418 provides the user with an indication of the direction that distal tip 93 of LG 92 is facing so that the user can control the advancement of the LG 92 in the patient's airways.

In step s314, the catheter is navigated through the bronchi. While the catheter is navigated through the bronchi, workstation 80 executes an MIP algorithm to calculate the MIP in a limited range from the distal tip 93 in step s316 and displays the MIP in step s318. The limited range may be predefined or be dynamically calculated based on a location of the target. For example, the limited range may be 35 mm from the distal tip 93. Limiting the MIP algorithm to highlight structures within the limited range of the distal tip 93 may reduce the load on processor 204. By using a limited range, denser structures that may obscure the lesion may be omitted permitting the lesion to be displayed. The MIP algorithm causes lesions within the limited range to be displayed in their maximal surface size permitting the user to aim for the center of the target. As shown in alignment view 402, the MIP algorithm may be tuned to highlight lesion-density tissue and filter out most other densities in the CT volume, creating a clearer picture in which lung lesions stand out over dark background. A marking 408, e.g., a green sphere or ellipsoid, may be used to represent the planned target and is overlaid on the rendered volume to reduce risk of aligning to the wrong object. A crosshair 410 in the center of the view assists the user in aligning distal tip 93 with the center of the target. The distance 412 from the distal tip 93 to the center of the marked target is displayed next to the crosshair 410, permitting the user to find the best balance between alignment and proximity.

In step s320, a determination is made as to whether the lesion is within the limited range. The determination may be made by a user or it may be determined using known image analysis techniques. If the lesion is not within the limited range of the distal tip 93, the process returns to step s314 where the user continues to navigate the catheter.

In the embodiments described herein, the alignment of the catheter using CT image data and 3D models permits a better aiming experience over other CT volume representations. Target areas of lesions may be shown from a distance, where a normal CT slice would not be useful. The target is shown at a limited range as opposed to normal MIP that may show more dense and distal objects that obscure the lesion. The embodiments permit a user to assess optimal balance between alignment/proximity, which defines the best location for biopsy tool introduction. The view looks similar to CT images thereby psychologically assuring physicians that the information they are looking at is real, permits aiming to various parts of the lesion structure, and assures users that they are at the planned target. In the 3D models, irrelevant structures in the range are minimized permitting the user to clearly identify the lesion.

Referring back to FIG. 1, catheter guide assemblies 90, 100 have different operating mechanisms, but each contain a handle 91 that can be manipulated by rotation and compression to steer the distal tip 93 of the LG 92, extended working channel 96. Catheter guide assemblies 90 are currently marketed and sold by Covidien LP under the name SUPERDIMENSION® Procedure Kits, similarly catheter guide assemblies 100 are currently sold by Covidien LP under the name EDGE™ Procedure Kits, both kits include a handle 91, extended working channel 96, and locatable guide 92. For a more detailed description of the catheter guide assemblies 90, 100 reference is made to commonly-owned U.S. patent application Ser. No. 13/836,203 filed on Mar. 15, 2013 by Ladtkow et al., the entire contents of which are hereby incorporated by reference.

As illustrated in FIG. 1, the patient is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50.

Catheter guide assemblies 90, 100 including LG 92 and EWC 96 are configured for insertion through a working channel of bronchoscope 50 into the patient's airways (although the catheter guide assemblies 90, 100 may alternatively be used without bronchoscope 50). The LG 92 and EWC 96 are selectively lockable relative to one another via a locking mechanism 99. A six degrees-of-freedom electromagnetic tracking system 70, e.g., similar to those disclosed in U.S. Pat. No. 6,188,355 and published PCT Application Nos. WO 00/10456 and WO 01/67035, the entire contents of each of which is incorporated herein by reference, or any other suitable positioning measuring system, is utilized for performing navigation, although other configurations are also contemplated. Tracking system 70 is configured for use with catheter guide assemblies 90, 100 to track the position of the EM sensor 94 as it moves in conjunction with the EWC 96 through the airways of the patient, as detailed below.

As shown in FIG. 1, electromagnetic field generator 76 is positioned beneath the patient. Electromagnetic field generator 76 and the plurality of reference sensors 74 are interconnected with tracking module 72, which derives the location of each reference sensor 74 in six degrees of freedom. One or more of reference sensors 74 are attached to the chest of the patient. The six degrees of freedom coordinates of reference sensors 74 are sent to workstation 80, which includes application 81 where sensors 74 are used to calculate a patient coordinate frame of reference.

Also shown in FIG. 1 is a catheter biopsy tool 102 that is insertable into the catheter guide assemblies 90,100 following navigation to a target and removal of the LG 92. The biopsy tool 102 is used to collect one or more tissue sample from the target tissue. As detailed below, biopsy tool 102 is further configured for use in conjunction with tracking system 70 to facilitate navigation of biopsy tool 102 to the target tissue, tracking of a location of biopsy tool 102 as it is manipulated relative to the target tissue to obtain the tissue sample, and/or marking the location where the tissue sample was obtained.

Although navigation is detailed above with respect to EM sensor 94 being included in the LG 92 it is also envisioned that EM sensor 94 may be embedded or incorporated within biopsy tool 102 where biopsy tool 102 may alternatively be utilized for navigation without need of the LG or the necessary tool exchanges that use of the LG requires. A variety of useable biopsy tools are described in U.S. Provisional Patent Application Nos. 61/906,732 and 61/906,762 both entitled DEVICES, SYSTEMS, AND METHODS FOR NAVIGATING A BIOPSY TOOL TO A TARGET LOCATION AND OBTAINING A TISSUE SAMPLE USING THE SAME, filed Nov. 20, 2013 and U.S. Provisional Patent Application No. 61/955,407 having the same title and filed Mar. 14, 2014, the entire contents of each of which are incorporated herein by reference and useable with the EMN system 10 as described herein.

During procedure planning, workstation 80 utilizes computed tomographic (CT) image data for generating and viewing a three-dimensional model ("3D model") of the patient's airways, enables the identification of target tissue on the 3D model (automatically, semi-automatically or manually), and allows for the selection of a pathway through the patient's airways to the target tissue. More specifically, the CT scans are processed and assembled into a 3D volume, which is then utilized to generate the 3D model of the patient's airways. The 3D model may be presented on a display monitor 81 associated with workstation 80, or in any other suitable fashion. Using workstation 80, various slices of the 3D volume and views of the 3D model may be presented and/or may be manipulated by a clinician to facilitate identification of a target and selection of a suitable pathway through the patient's airways to access the target. The 3D model may also show marks of the locations where previous biopsies were performed, including the dates, times, and other identifying information regarding the tissue samples obtained. These marks may also be selected as the target to which a pathway can be planned. Once selected, the pathway is saved for use during the navigation procedure. An example of a suitable pathway planning system and method is described in U.S. patent application Ser. Nos. 13/838,805; 13/838,997; and 13/839,224, filed on Mar. 15, 2014, the entire contents of each of which are incorporated herein by reference.

During navigation, EM sensor 94, in conjunction with tracking system 70, enables tracking of EM sensor 94 and/or biopsy tool 102 as EM sensor 94 or biopsy tool 102 is advanced through the patient's airways.

Referring back to FIG. 2, memory 202 includes any non-transitory computer-readable storage media for storing data and/or software that is executable by processor 204 and which controls the operation of workstation 80. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 80.

Memory 202 may store application 81 and/or CT data 214. Application 81 may, when executed by processor 204, cause display 206 to present user interface 216. Network interface 208 may be configured to connect to a network such as a local area network (LAN) consisting of a wired network and/or a wireless network, a wide area network (WAN), a wireless mobile network, a Bluetooth network, and/or the internet. Input device 210 may be any device by means of which a user may interact with workstation 80, such as, for example, a mouse, keyboard, foot pedal, touch screen, and/or voice interface. Output module 212 may include any connectivity port or bus, such as, for example, parallel ports, serial ports, universal serial busses (USB), or any other similar connectivity port known to those skilled in the art.

Any of the herein described methods, programs, algorithms or codes may be converted to, or expressed in, a programming language or computer program. A "Programming Language" and "Computer Program" is any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. For the purposes of this definition, no distinction is made between languages which are interpreted, compiled, or use both compiled and interpreted approaches. For the purposes of this definition, no distinction is made between compiled and source versions of a program. Thus, reference to a program, where the programming language could exist in more than one state (such as source, compiled, object, or linked) is a reference to any and all such states. The definition also encompasses the actual instructions and the intent of those instructions.

Further aspects of image and data generation, management, and manipulation useable in either the planning or navigation phases of an ENB procedure are more fully described in commonly-owned U.S. Provisional Patent Application Ser. No. 62/020,220 entitled "Real-Time Automatic Registration Feedback," filed on Jul. 2, 2014, by Brown et al.; U.S. Provisional Patent Application Ser. No. 62/020,177 entitled "Methods for Marking Biopsy Location," filed on Jul. 2, 2014, by Brown; U.S. Provisional Patent Application Ser. No. 62/020,238 entitled "Intelligent Display," filed on Jul. 2, 2014, by Kehat et al.; U.S. Provisional Patent Application Ser. No. 62/020,242 entitled "Unified Coordinate System For Multiple Ct Scans Of Patient Lungs," filed on Jul. 2, 2014, by Greenburg; U.S. Provisional Patent Application Ser. No. 62/020,250 entitled "Algorithm for Fluoroscopic Pose Estimation," filed on Jul. 2, 2014, by Merlet; U.S. Provisional Patent Application Ser. No. 62/020,261 entitled "System and Method for Segmentation of Lung," filed on Jul. 2, 2014, by Markov et al.; U.S. Provisional Patent Application Ser. No. 62/020,253 entitled "Trachea Marking," filed on Jul. 2, 2014, by Lachmanovich et al.; U.S. Provisional Patent Application Ser. No. 62/020,257 entitled "Automatic Detection Of Human Lung Trachea," filed on Jul. 2, 2014, by Markov et al.; U.S. Provisional Patent Application Ser. No. 62/020,261 entitled "Lung And Pleura Segmentation," filed on Jul. 2, 2014, by Markov et al.; U.S. Provisional Patent Application Ser. No. 62/020,258 entitled "Cone View—A Method Of Providing Distance And Orientation Feedback While Navigating In 3d," filed on Jul. 2, 2014, by Lachmanovich et al.; and U.S. Provisional Patent Application Ser. No. 62/020,262 entitled "Dynamic 3D Lung Map View for Tool Navigation Inside the Lung," filed on Jul. 2, 2014, by Weingarten et al., the entire contents of all of which are hereby incorporated by reference.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A system for navigating to a target through a patient's bronchial tree, the system comprising:
a bronchoscope configured for insertion into the patient's bronchial tree, the bronchoscope defining a working channel;
a probe insertable into the working channel of the bronchoscope and configured to navigate through the patient's bronchial tree, the probe including a sensor, the sensor configured to generate location information and pose information; and
a workstation in operative communication with the probe and the bronchoscope, the workstation including a memory and at least one processor, the memory storing a navigation plan and a program that, when executed by the processor, causes the workstation to:
receive the location information and the pose information,
execute a maximum intensity projection (MIP) algorithm for a range from a distal tip of the sensor according to the location information and the pose information,
present a user interface that guides a user through the navigation plan, the user interface configured to present:
a three-dimensional (3D) view for displaying a 3D rendering of the patient's airways and a display of the navigation plan;
a local view for assisting the user in navigating the probe through peripheral airways of the patient's bronchial tree to the target; and
an alignment view for assisting the user in aligning a distal tip of the probe with the target, the alignment view including an image generated from the execution of the MIP algorithm.

2. The system according to claim 1, wherein the range is predetermined.

3. The system according to claim 1, wherein the range is dynamically calculated based on a location of the target.

4. The system according to claim 1, wherein the MIP algorithm highlights the target and filters out densities of other tissue near the target.

5. The system according to claim 1, wherein the alignment view presents a marking overlaid on the target.

6. The system according to claim 1, wherein the alignment view presents a crosshair to assist alignment to a center of the target.

7. The system according to claim 1, wherein the alignment view presents a distance from a tip of the sensor to the target.

8. A system for navigating to a target through a patient's bronchial tree, the system comprising:
a bronchoscope configured for insertion into the patient's bronchial tree, the bronchoscope defining a working channel;
a probe insertable into the working channel of the bronchoscope and configured to navigate through the patient's bronchial tree, the probe including a sensor, the sensor configured to generate location information and pose information; and
a workstation in operative communication with the probe and the bronchoscope, the workstation including a memory and at least one processor, the memory storing a navigation plan and a program that, when executed by the processor, causes the workstation to:
receive the location information and the pose information,
execute a maximum intensity projection (MIP) algorithm for a range from a distal tip of the sensor according to the location information and the pose information,
presents a user interface that guides a user through the navigation plan, the user interface configured to present an alignment view for assisting the user in aligning a distal tip of the probe with the target, wherein the range from the distal tip of the sensor is a limited range from the distal tip of the sensor.

9. The system according to claim 8, wherein the limited range is predetermined.

10. The system according to claim 8, wherein the limited range is dynamically calculated based on a location of the target.

11. The system according to claim 8, wherein the MIP algorithm highlights the target and filters out densities of other tissue near the target.

12. The system according to claim 8, wherein the alignment view presents a marking overlaid on the target.

13. The system according to claim 8, wherein the alignment view presents a crosshair to assist alignment to a center of the target.

14. The system according to claim 8, wherein the alignment view presents a distance from a tip of the sensor to the target.

\* \* \* \* \*